United States Patent [19]

Davis

[11] Patent Number: 4,648,204
[45] Date of Patent: Mar. 10, 1987

[54] PROCESS FOR FORMING SEEDS CAPABLE OF GROWING HYBRID SOYBEAN PLANTS

[75] Inventor: William H. Davis, Plainview

[73] Assignee: Ring Around Products, Inc., Prattville, Ala.

[21] Appl. No.: 779,647

[22] Filed: Sep. 24, 1985

Related U.S. Application Data

[63] Continuation-in-part of Ser. No. 585,940, Mar. 5, 1984, Pat. No. 4,545,146.

[51] Int. Cl.$^4$ ............................................. A01H 1/02
[52] U.S. Cl. .................................... 47/58; 47/DIG. 1
[58] Field of Search ............................ 47/58, DIG. 1

[56] References Cited

U.S. PATENT DOCUMENTS

| | | | |
|---|---|---|---|
| 3,903,645 | 9/1975 | Bradner | 47/58 |
| 4,077,157 | 3/1978 | Bradner | 47/58 |
| 4,517,763 | 5/1985 | Beversdorf et al. | 47/58 |

OTHER PUBLICATIONS

"A Partially Male Sterile Strain of Soybeans", by C. E. Caviness, H. J. Walters and D. L. Johnson, Crop Science, vol. 10, pp. 107–108 (Jan.–Feb., 1970).
"Inheritance of a Male-Sterile Character in Soybeans", C. A. Brim and M. F. Young, Crop Science, vol. 11, pp. 564–566 (Jul.–Aug., 1971).
"Influence of Temperature on a Partially Male-Sterile Soybean Strain", by C. E. Caviness and B. L. Fagala, Crop Science, vol. 13, pp. 503–504 (Sep.–Oct., 1973).
"Implications of Male-Sterility in Soybeans", by A. Brim, Proceedings of the Sixth Soybean Seed Research Conference–1976, pp. 67–71.
"Technology of Hybrid Soybeans", by W. H. Davis, Proceedings of the Sixth Soybean Seed Research Conference–1976, pp. 72–74.
"A New Male-Sterile Strain in Wabash Soybeans", by H. K. Chaudhari and W. H. Davis, J. of Heredity, vol. 68, pp. 266–267 (1977).
"Pollen Production in Soybeans with Respect to Genotype, Environment, and Stamen Position", by R. G. Palmer, M. C. Albertson and H. Heer, Euphytica, vol. 27, pp. 427–433 (1978).
"Genetics and Cytology of the $ms_3$ Male-Sterile Soybean", by R. G. Palmer, C. W. Johns and P. S. Muir, J. of Heredity, vol. 71, pp. 343–348 (1980).
"Pollination of Male-Sterile Soybeans in Caged Plots", by P. D. Koelling, W. J. Kenworthy and D. M. Caron, Crop Science, vol. 21, pp. 559–561 (Jul.–Aug., 1981).
"Variable Development in Anthers of Partially Male-Sterile Soybeans", by D. M. Stelly and R. G. Palmer, J. of Heredity, vol. 73, pp. 101–108 (1982).
"Genetics and Cytology of the $ms_4$ Male-Sterile Soybean", by X. Delanney and R. G. Palmer, J. of Heredity, vol. 73, pp. 219–223 (1982).
"Application of Genetic Male Sterility to Recurrent Selection Schemes in Soybeans", C. A. Brim and C. W. Struber, Crop Science, vol. 13, pp. 528–530, (Sep.–Oct., 1973).
"Genetics and Ultrastructure of a Cytoplasmically Inherited Yellow Mutant in Soybeans", by Reid G. Palmer and Peter N. Mascia, Genetics, vol. 95, pp. 985–1000 (Aug., 1980).
"Plant Stress and Water Conservation Research Program: A Progress Report", published by the College of Argicultural Sciences, Texas Tech University, Lubbock, Texas, at p. 7 (map) (1984).
"Soybeans: Improvement, Production, and Uses", Chapter 6, by Edgar E. Hartwig, American Society of Agronomy, Inc., pp. 189–190 (1973).

*Primary Examiner*—Robert E. Bagwill
*Attorney, Agent, or Firm*—Burns, Doane, Swecker & Mathis

[57] ABSTRACT

An improved process is provided for forming seeds capable of yielding $F_1$ hybrid soybean plants (i.e., hybrid soybean plants of the first filial generation) or maintaining male sterile soybean plants useful in the production of male fertile $F_1$ hybrid soybean plants. Male sterile soybean plants (i.e., seed parents) and the male fertile soybean plants (i.e., pollen parents) are caused to undergo cross-pollination with the aid of pollen-carrying bees under conditions wherein pollen transport from the male parents to the female parents is significantly increased. Such pollen transfer is enhanced by growing the parent soybean plants at a location where natural rainfall is limited when soybean flowering occurs during the summer, applyng water via irrigation as required to promote normal plant growth up to at least the time of the onset of flower formation, and withholding irrigation water at the appropriate time to induce enhanced nectar flow within the soybean flowers and render the soybean flowers highly attractive to bees. In accordance with the concept of the present invention the pollen-carrying bees (e.g., honeybees) which are strongly attracted to the enhanced nectar flow within the soybean flowers concomitantly facilitate a high level of cross-pollination and seeds are formed on the male sterile soybean plants which ultimately are harvested.

112 Claims, No Drawings

4,648,204

PROCESS FOR FORMING SEEDS CAPABLE OF GROWING HYBRID SOYBEAN PLANTS

CROSS-REFERENCE TO RELATED APPLICATION

This is a continuation-in-part of my U.S. Ser. No. 585,940, filed Mar. 5, 1984 (now U.S. Pat. No. 4,545,146), and entitled "Improved Route to Hybrid Soybean Production."

BACKGROUND OF THE INVENTION

It is well known that when different plant lines are cross-pollinated one can achieve in the offspring a highly desirable heterosis or hybrid vigor which advantageously provides increased yields of the desired crop.

Soybeans (i.e., seeds of *Glycine max* plants) are recognized to be an important crop in many parts of the world. For instance, approximately 65 to 75 million acres of soybeans are planted annually in the United States which establishes this to be the largest seed crop presently grown in the United States. Various approaches to the production of hybrid soybeans are disclosed in U.S. Pat. Nos. 3,903,645 and 4,077,157, and in my copending U.S. Ser. No. 585,940, filed Mar. 5, 1984 (now U.S. Pat. No. 4,545,146). Also, technical articles which discuss the existance of some degree of sterility in soybeans and the formation of hybrid soybean seeds are identified in my copending U.S. Ser. No. 585,940, filed Mar. 5, 1984 (now U.S. Pat. No. 4,545,146), and are herein incorporated by reference.

It is an object of the present invention to provide an improved process for producing seeds capable of forming $F_1$ hybrid soybean plants wherein pollen-carrying bees are employed to accomplish the required pollen transfer.

It is an object of the present invention to provide an improved process for maintaining male sterile soybean plants useful in the production of male fertile $F_1$ hybrid soybean plants wherein pollen-carrying bees are employed to accomplish the required pollen transfer.

It is an object of the present invention to provide an improved process for producing seeds capable of forming $F_1$ hybrid soybean plants wherein the required visitation between the parent plants by pollen-carrying bees is promoted on a highly effective basis.

It is another object of the present invention to provide an improved process for maintaining male sterile soybean plants useful in the production of male fertile $F_1$ hybrid soybean plants wherein the required visitation between the parent plants by pollen-carrying bees is promoted on a highly effective basis.

It is a further object of the present invention to provide an improved process for producing seeds capable of forming $F_1$ hybrid soybean plants wherein the seed product is caused to set in increased yields.

These and other objects as well as the scope, nature, and utilization of the claimed invention will be apparent to those skilled in the art from the following detailed description and appended claims.

SUMMARY OF THE INVENTION

It has been found that an improved process for the efficient production of seeds capable of growing $F_1$ hybrid *Glycine max* comprises:

(a) growing at a location which normally experiences limited natural rainfall when soybean flowering occurs during the summer a substantially uniform population of male sterile soybean plants in pollinating proximity to a substantially uniform population of male fertile soybean plants which when crossed with the male sterile soybean plants enable the formation of seeds on the male sterile soybean plants which are capable of growing male fertile $F_1$ hybrid soybean plants, (b) applying water via irrigation to the substantially uniform populations of soybean plants of step (a) as required to promote normal plant growth up to at least the time of the onset of flower formation within each of the populations, (c) withholding irrigation water from the plants of the substantially uniform populations at a time when flowers are present within each of the substantially uniform populations for a period of time during which no appreciable natural rainfall occurs so as to induce enhanced nectar flow within the flowers which serves to render the flowers more attractive to bees, (d) crossing the male sterile soybean plants and the male fertile soybean plants with the aid of pollen-carrying bees which are attracted to the enhanced nectar flow whereby seeds are formed on the male sterile soybean plants, and (e) selectively recovering the seeds which have formed on the substantially uniform population of male sterile soybean plants.

It has been found that an improved process for the efficient production of a binary seed blend containing a substantial proportion of seeds capable of growing male fertile $F_1$ hybrid *Glycine max* plants comprises:

(a) growing at a location which normally experiences limited natural rainfall when soybean flowering occurs during the summer a substantially random population of male sterile soybean plants and male fertile soybean plants which when crossed with the male sterile soybean plants enable the formation of seeds on the male sterile soybean plants which are capable of growing male fertile $F_1$ hybrid soybean plants, (b) applying water via irrigation to the substantially random population of soybean plants of step (a) as required to promote normal plant growth up to at least the time of the onset of flower formation, (c) withholding irrigation water from the plants of the substantially random population at a time when flowers are present for a period of time during which no appreciable natural rainfall occurs so as to induce enhanced nectar flow within the flowers which serves to render the flowers more attractive to bees, (d) pollinating the substantially random population of soybean plants with the aid of pollen-carrying bees which are attracted to the enhanced nectar flow whereby seeds are formed on the male sterile plants which are capable of growing male fertile $F_1$ hybrid soybean plants and seeds are formed on the male fertile soybean plants as a result of self-pollination, and (e) recovering seeds which have formed on the substantially random population of soybean plants.

It has been found that an improved process for maintaining male sterile *Glycine max* plants useful in the production of male fertile $F_1$ hybrid soybean plants comprises:

(a) growing at a location which normally experiences limited natural rainfall when soybean flowering occurs during the summer a substantially uniform population of cytoplasmically male sterile soybean plants in pollinating proximity to a substantially uniform population of male fertile maintainer soybean plants which when crossed with the cytoplasmically male sterile soybean plants enable the formation of seeds on the cytoplasmically male sterile plants which are capable of growing additional cytoplasmically male sterile plants, (b) applying water via irrigation to the substantially uniform populations of soybean plants of step (a) as required to promote normal plant growth up to at least the time of the onset of flower formation within each of the populations, (c) withholding irrigation water from the plants of the substantially uniform populations at a time when flowers are present within each of the substantially uniform populations for a period of time during which no appreciable natural rainfall occurs so as to induce enhanced nectar flow within the flowers which serves to render the flowers more attractive to bees, (d) crossing the cytoplasmically male sterile soybean plants and the male fertile maintainer soybean plants with the aid of pollen-carrying bees which are attracted to the enhanced nectar flow whereby seeds are formed on the male sterile soybean plants, and (e) selectively recovering the seeds which have formed on the substantially uniform population of cytoplasmically male sterile soybean plants.

DETAILED DESCRIPTION OF THE INVENTION

In accordance with the concept of the present invention it is essential that the parent soybean plants be grown at a location which normally experiences limited natural rainfall during the summer months when soybean flowers normally are formed and cross-pollination is carried out with the aid of pollen-carrying bees. Natural rainfall when soybean flowers are present can adversely impact upon the enhanced nectar flow within the soybean flowers made possible in the improved process of the present invention. Accordingly, the location where the process of the present invention is carried out generally will be different than those areas where soybean plants customarily have been grown in the past. For instance, the bulk of those areas of the United States previously devoted to the growing of soybeans for commercial crops and seeds will be unsuitable for hybrid seed production in accordance with the concept of the present invention. If the planting area experiences significant rainfall during the summer months when soybean flowers are present, this will introduce an element of unpredictability which will make it infeasible to attempt to implement the concept of the present invention. Such rainfall at an inappropriate time will destroy the highly effective enhanced pollen transfer among soybean plants as provided herein.

The location selected for growing the soybean plants may be one which experiences (1) limited natural rainfall throughout the entire year, or (2) limited natural rainfall during the summer months when soybean flowering capable of producing cross-pollination occurs (i.e., soybean flowers are present on each parent) and more plentiful rainfall at other times during the year.

In a preferred embodiment of the present invention the location selected to grow the soybean parent plants will normally experience less than 4 inches of rainfall when soybean flowering occurs during the summer (i.e., the average natural rainfall for the past 10 years will be less than 4 inches when soybean flowering simultaneously occurs on each parent during the 3 summer months). In a particularly preferred embodiment of the present invention the location selected to grow the soybean parent plants will normally experience less than 2 inches of rainfall (e.g., less than 1 inch of rain) when soybean flowering occurs during the summer (i.e., the average natural rainfall for the past 10 years will be less than 2 inches when soybean flowering simultaneously occurs on each parent during the 3 summer months).

In the United States the improved process of the present invention commonly will be carried out in relatively dry areas which are generally west of those where soybean plants customarily are grown. For instance, limited areas from within the Great Plains may be selected extending from South Dakota, eastern Wyoming, Nebraska, eastern Colorado, western Kansas, the Oklahoma panhandle, eastern New Mexico and western Texas which commonly are irrigated from the vast underground Ogallala Aquifer. See, "Plant Stress and Water Conservation Research Program: A Progress Report" published by the College of Agricultural Sciences, Texas Tech University, Lubbock, Tex. (1984) at Page 7 for a map which illustrates the location of the Ogallala Aquifer and which is herein incorporated by reference. The drier areas of Nebraska, Kansas, and western Texas are particularly suited for carrying out the improved process of the present invention.

Representative counties served by the Ogallala Aquifer where the process of the present invention can be carried out to particular advantage include the South Dakota counties of Shannon, Bennett, Todd, Tripp, Gregory, and Gillette; the Wyoming counties of Converse, Laramie, Platte, Goshen, and Niobrara; the Nebraska counties of Dawes, Box Butte, Garden, Kimball, Morrill, Cheyenne, Sheridan, Banner, Scotts Bluff, Keith, Arthur, McPherson, Grant, Cherry, Hooker, Thomas, Deuel, Keya Paha, Perkins, Chase, Dundy, Hitchcock, Red Willow, Hayes, Frontier, Lincoln, Logan, Loup, Garfield, Holt, Rock, Valley, Greely, Sherman, Howard, Buffalo, Hall, Gosper, Phelps, Kearney, Furnas, Harlan, Franklin, Webster, Adams, Wheeler, Antelope, and Boone; the Colorado counties of Sedgwick, Phillips, Logan, Weld, Morgan, Washington, Yuma, Kit Carson, Cheyenne, Kiowa, Prowers, Baca, Las Animas, Bent, Otero, Crowley, and Lincoln; the Kansas counties of Cheyenne, Rawlins, Sherman, Thomas, Decatur, Sheridan, Norton, Phillips, Graham, Wallace, Logan, Greeley, Wichita, Scott, Ness, Hamilton, Kearney, Finney, Stanton, Grant, Haskell, Gray, Ford, Hodgman, Morton, Stevens, Seward, Mead, Clark, Kiowa, Comanche, Edwards, Pawnee, Pratt, Stafford, Barton, Rice, Reno, Kingman, McPhereson, Harvey, and Sedgwick; the Oklahoma counties of Cimarron, Texas, Beaver, Harper, Woodward, Roger Mills, and Dewey; the New Mexico counties of Curry, Roosevelt, Chaves, Lea, and Quay; and the Texas counties of Hartley, Dallam, Sherman, Moore, Hansford, Hutchinson, Carson, Roberts, Hemphill, Gray, Wheeler, Deaf Smith, Randall, Armstrong, Donley, Parmer, Castro, Swisher, Briscoe, Bailey, Lamb, Hale, Floyd, Motley, Cochran, Hockley, Lubbock, Crosby, Dickens, Yoakum, Terry, Lynn, Garza, Gaines, Dawson, Andrews, Martin, Mitchell, Ector, Midland, and Glasscock.

The thirteen counties of northeastern Arkansas (i.e., Clay, Craighead, Cross, Crittenden, Greene, Independence, Jackson, Lawrence, Mississippi, Poinsett, Randolph, White and Woodruff) are well suited for carrying out the process of the present invention since rainfall normally is limited at that location during the summer months.

Other illustrative areas in the United States where the process of the present invention conveniently can be practiced include the irrigated areas of Idaho, Oregon, Washington, California, etc.

Illustrative areas outside of the United States where the process of the present invention conveniently can be practiced include Argentina, Brazil, Chile, Mexico, Canada, Egypt, South Africa, Sudan, Turkey, U.S.S.R., India, Peoples' Republic of China, Australia, New Zealand, etc.

It should be understood, however, that the process of the present invention can be carried out at any location in the northern or southern hemispheres where the soil will support the growth of soybean plants, limited rainfall occurs during the summer, and irrigation water is available to promote normal plant growth.

It is preferred that the area selected be one in which there is a relatively low pesticide usage, honeybees customarily are kept and are available, and a wild bee population is available.

The key parent soybean plants which are grown in accordance with the concept of the present invention are male sterile soybean plants that serve as the seed parents and male fertile soybean plants that serve as the pollen parents. The male sterile soybean plants are fully female fertile, but yield no viable pollen that produces unwanted self-pollination. These male sterile soybean plants serve as the female parents following the required cross-pollination. Accordingly, all of the seed formed on the male sterile soybean plants following pollination will be capable of forming the desired soybean plants. The male sterility of the male sterile soybean plants can be of varied causation. For instance, such plants may be cytoplasmically male sterile or genetically male sterile. Alternatively, such plants may be rendered male sterile through the application of a chemical which destroys the ability of the plants to yield viable pollen (i.e., a gametocide). Representative gametocides include FW450 available from Rohm & Haas Co., TD-1123 available from Pennwalt Corp., potassium 3,4-dichloro-5-isothiazolecarboxylate, 2,3-dichloroisobutyric acid and the water soluble salts hereof (e.g., sodium 2,3-dichloroisobutyrate available from Rohm & Haas Co.), etc.

In accordance with a preferred embodiment of the present invention, the male sterile plants are cytoplasmically male sterile plants as described in my copending U.S. Ser. No. 585,940 filed on Mar. 5, 1984 (now U.S. Pat. No. 4,545,146), which is herein incorporated by reference. As described in such copending Application, three factors found to exist in available sources of *Glycine max* plants, when properly combined in a single plant by the intervention of man, provide an effective starting plant to accomplish the hybrid soybean production. Such factors (as described hereafter) have heretofore existed separately while dispersed in soybean plants from widely differing sources. The female fertile male sterile soybean plants possess (1) a Cms cytoplasm, (2) a distinct pair of recessive $r_1r_1$ genes in the cell nucleus, and (3) a distinct pair of recessive $r_2r_2$ genes in the cell nucleus, which in combination render the plant incapable of producing viable pollen while otherwise carrying out the usual plant functions required to produce soybeans if viable pollen is provided from another soybean plant.

*Glycine max* plants are self-destructing annuals which cannot be satisfactorily propagated by asexual means since if new plants are formed by cuttings, the new plants are of a progressively smaller size. The preferred female fertile male sterile soybean plants can be successfully propagated (i.e., maintained) by sexual means as described hereafter. Also, these male sterile plants unlike soybean plants which rely exclusively on nuclear genes for sterility can be conveniently perpetuated or maintained without unwanted segregation with respect to sterility, as described hereafter.

The atypical Cms cytoplasm of the preferred female fertile male sterile soybean plants can be derived through the female parent from an appropriate cytoplasmic source. For instance, it has been found that the Cms cytoplasm required in the female fertile fully male sterile soybean plants can be conveniently derived from a Mandarin cytoplasmic source through the female parent. Many Northern soybean varieties are derived from this cytoplasmic source. Plants of this origin have been found inherently to possess an atypical cytoplasm of the type required to practice the present invention. Since this required factor is not contributed by nuclear genes and is not transmitted through the pollen, it can be considered cytoplasmic, non-Mendelian, extrachromosomal, uniparental, and maternal. Representative commercially available soybean plants which are derived maternally from a Mandarin cytoplasmic source are Adelphia, Chippewa, Chippewa 64, Clark, Classic I, Classic II, Columbus, Cutler, Disoy, Elf, Ford, Grant, Harosoy, Harosoy 63, Hobbitt, Kent, Lincoln, Lindarin, Lindarin 63, Magna, Prize, Provar, Rampage, RA 203, RA 402, RA 481, RAX 56, RAX 57, RAX 61, RAX 62, RAX 66, SB 27, Shelby, Traverse, Wayne, Wirth, Williams, etc. A particularly good source for the required Cms cytoplasm has been found to be the Elf variety which was introduced during 1977 by AR-SEA-USDA, the Ohio Agric. Res. and Dev. Center, and the U. of Illinois Agric. Res. Station. In 1981 this variety was registered by the Crop Sci. Soc. of Am. as Reg. No. 150.

It should be emphasized that when plants of the above-identified varieties are inspected for the possible absence of viable pollen production, that male sterile plants (either partially male sterile or completely male sterile) wherein the sterility is attributable to the cytoplasm are not observed. It has been found that such sterility is not expressed even though the required atypical Cms cytoplasm is present because it is not in combination with the required recessive genes discussed hereafter. Instead such varieties can be shown to possess at least one pair of dominant $R_1R_1$ or $R_2R_2$ genes (usually both pairs) which always leads to the expression of the usual viable pollen production even in the presence of the Cms cytoplasm.

The pair of recessive genes $r_1r_1$ for male sterility present in the preferred female fertile fully male sterile plants employed in the process of the present invention can be derived through its male parent from a first gene source which possesses such genes. Unlike the male sterile plants, the first gene source may possess a usual N cytoplasm which can be termed a "normal" or "neutral" cytoplasm. When such cytoplasm is present, cytoplasmically controlled male sterility is not exhibited regardless of the nuclear genes which are present.

It has been found that the requisite pair of $r_1r_1$ recessive genes in the cell nucleus of the female fertile fully male sterile soybean plants conveniently can be derived through the male parent from a Dunfield germplasm base. Many Southern soybean varieties are derived from this germplasm base. Plants of this origin have been found inherently to possess the required pair of recessive genes which has been designated $r_1r_1$. Representative commercially available soybean plants from which the $r_1r_1$ recessive genes may be derived are Bedford, Bethel, Centennial, Dare, Dyer, Forrest, Hill, Kirby, RA(d)41, RA 581, RA 603, RA 605, RA 606, RA 680, Tracy, Wabash, York, etc. A particularly good source for the $r_1r_1$ recessive genes has been found to be the Bedford variety which was introduced during 1978 by FR-SEA-USDA, and the Tennessee and Mississippi Agric. Expt. Stations. This variety was registered by the Crop Sci. Soc. of Am. as Reg. No. 118.

It further should be emphasized that when plants of the above-identified varieties having $r_1r_1$ genes are inspected for the possible absence of viable pollen production, that male sterile plants (either partially male sterile or completely male sterile) wherein the sterility is attributable to the cytoplasm are not observed. It has been found that such sterility will not be expressed unless the atypical Cms cytoplasm is present along with recessive genes $r_2r_2$. Instead such varieties can be shown to possess dominant $R_2R_2$ genes which restore male fertility.

The pair of recessive genes $r_2r_2$ for male sterility present in the preferred female fertile fully male sterile plants can be derived through its male parent from a second gene source which possesses such genes. Such $r_2r_2$ genes are present as a distinct gene pair apart from the $r_1r_1$ genes in the female fertile fully male sterile plants (i.e., they are present at different loci). Unlike the male sterile plants, the second gene source may possess a usual N cytoplasm which can be termed a "normal" or "neutral" cytoplasm. As previously indicated, when such cytoplasm is present cytoplasmically controlled male sterility is not exhibited regardless of the nuclear genes which are present.

It has been found that the requisite pair of $r_2r_2$ recessive genes in the cell nucleus of the perferred female fertile fully male sterile soybean plants conveniently can be derived through the male parent from a Tokyo germplasm base. Many Southern soybean varieties are derived from this germplasm base. Plants of this origin have been found inherently to possess the required pair of recessive genes which has been designated $r_2r_2$. Representative commercially available soybean plants from which the $r_2r_2$ recessive genes may be derived are Bragg, Braxton, Cobb, Govan, Hampton, Hampton 266, Hardee, Hutton, Jackson, Kirby, Majos, Ogden, RA 604, RA 701, RA 800, Volstate, Wright, etc. A particularly good source for the $r_2r_2$ recessive genes has been found in the Braxton variety which was introduced during 1979 by the USDA and various state Agric. Expt. Stations.

It additionally should be emphasized that when plants of the above-identified varieties having $r_2r_2$ genes are inspected for the possible absence of viable pollen production, that male sterile plants (either partially male sterile or completely male sterile) wherein the sterility is attributable to the cytoplasm are not observed. It has been found that such sterility will not be expressed unless the atypical Cms cytoplasm is present along with recessive genes $r_1r_1$. Instead such varieties can be shown to possess dominant $R_1R_1$ genes which restore male fertility.

The preferred female fertile fully male sterile plants can be maintained or perpetuated in spite of the male sterility by crossing with pollen from a soybean plant which possesses an N cytoplasm and the two distinct pairs of recessive genes $r_1r_1$ and $r_2r_2$. Such preferred maintainer plants are formed by the intervention of man through the combination of the required factors and are not found in nature. The progeny of this cross will again be female fertile and fully male sterile. Also, should the perferred female fertile fully male sterile plants be crossed with pollen from a male fertility restorer (i.e., having dominant $R_1R_1$ genes and/or dominant $R_2R_2$ genes), then the progeny will be fully fertile $F_1$ hybrid soybean plants. Suitable male fertility restorer plants are readily available without modification. For instance, any of the varieties heretofore named can perform this function. The only requirement is that plants which supply the pollen possess at least one pair of the required dominant fertility restoring genes.

The development of preferred female fertile fully male sterile soybean plants for use in the present invention, as well as preferred maintainer plants for the same, can be exemplified through a plant breeding program employing plants of the Elf, Bedford, and Braxton varieties. It should be understood, however, that the preferred embodiment of the present process can be equally well practiced through the utilization of soybean plants of other varieties provided the essential criteria set forth herein nevertheless are met. Initially plants of the Bedford variety (i.e., having an $r_1r_1$ gene source) are crossed by hand with pollen from plants of the Braxton variety (i.e., having an $r_2r_2$ gene source). The progeny of this cross are fully female fertile and male fertile and serve as a pollen source for plants of the Elf variety (i.e., having a Cms cytoplasmic source). Such crossing to the Elf variety is again carried out by hand under controlled conditions in the absence of Elf self-pollination. When the $F_1$ seed which has formed on the Elf female parent is grown, it will be noted that all of the resulting plants are fully female fertile and male fertile. Each of these $F_1$ plants is next self-pollinated through succeeding generations to form $F_2$, $F_3$, and $F_4$ controlled populations which are inspected for the absence of viable pollen. It is observed that some plants are female fertile fully male fertile, some plants are female fertile partially male fertile (i.e., produce only a limited quantity of viable pollen), and some plants are female fertile fully male sterile (i.e., produce no viable pollen).

The fact that none of the $F_1$ plants were male sterile in this preferred embodiment confirms that the sterility subsequently observed was not controlled solely by nuclear genes. The ratios in which the plants segregate in the $F_2$, $F_3$ and $F_4$ generations with respect to male sterility confirm that the sterility is cytoplasmic in nature and the result of a more complex cytoplasmic/genetic system in which the genetic aspect is bifactorial (i.e., two distinct gene pairs at different loci are operative and are interacting with the cytoplasm). The fully male sterile plants possess the Cms cytoplasm and the $r_1r_1$ and $r_2r_2$ genes. The partially male sterile plants possess the Cms cytoplasm and (1) $R_1r_1$ and $r_2r_2$ genes or (2) $r_1r_1$ and $R_2r_2$ genes. The fully male fertile plants possess the Cms cytoplasm and $R_1R_1$ genes and/or $R_2R_2$ genes. When the fully male sterile plants are crossed with pollen from the Elf, Bedford, and Braxton varieties, all $F_1$ progeny are fully male fertile. Accordingly, this indicates that no single parent variety (i.e., Elf, Bedford, or Braxton) possesses sufficient genes to create male sterile $F_1$ plants.

Once the preferred male sterile plants are on hand, suitable maintainer plants (i.e., those having an N cytoplasm in combination with $r_1r_1$ and $r_2r_2$ genes) can be developed by standard plant breeding techniques involving intercrossing and introgression. For instance, the required $r_1r_1$ and $r_2r_2$ genes can be provided in existing soybean varieties of agronomic importance having the usual N cytoplasm by intercrossing and possible backcrossing by hand with the pollen derived from female fertile partially male fertile plants obtained from the $F_2$, $F_3$ and $F_4$ controlled populations obtained during or subsequent to the development of the male sterile plants (described above). The $F_1$ plants from this cross are grown and are self-pollinated to form $F_2$ plants. Test crosses of the fully male sterile plants previously developed with pollen derived from the $F_2$ plants are made and those plants are identified and preserved which are capable of yielding fully male sterile $F_1$ progeny. Such plants possess the full complement of recessive $r_1r_1$ and $r_2r_2$ genes. Once identified such preferred homozygous maintainer plants can be perpetuated by self-pollination.

When producing seeds capable of growing male fertile $F_1$ hybrid soybean plants in accordance with one embodiment of the process of the present invention, the required male sterile soybean plants are grown at an appropriate location as a substantially uniform population in pollinating proximity to a substantially uniform population of male fertile soybean plants. In the context of the present invention "pollinating proximity" specifies that the two types of parent plants are sufficiently near that pollen can be transferred by pollen-carrying bees without loss of its viability. The male fertile soybean plants conveniently can be a pure line variety. For instance, the two types of plants can be grown adjacent to each other as alternating strips. In a preferred embodiment approximately 2, 4, or 6 rows of the male sterile soybean plants form a substantially uniform population and alternate with a substantially uniform population of approximately 2 rows of the male fertile soybean plants. Following pollen transfer from the male fertile soybean plants to the male sterile plants (as described hereafter), seeds are formed on the male sterile soybean plants. The male fertile soybean plants commonly are self-pollinated and seeds also form on them. At harvest time the seeds are selectively recovered from each of the substantially uniform plant populations. Accordingly, the seeds which are recovered from the male sterile soybean plants are a substantially homogeneous assemblage of seeds which upon growth yield male fertile $F_1$ hybrid soybean plants.

In accordance with another embodiment of the process of the present invention, a substantially uniform binary seed blend is formed containing a substantial proportion (e.g., at least one-half by number) of seeds capable of growing male fertile $F_1$ hybrid soybean plants. Such blend can be formed by growing at an appropriate location a substantially random population of male sterile soybean plants together with the male fertile soybean plants. For instance, approximately 75 to 95 percent (e.g., approximately 90 percent) of the plants in the random population can be male sterile plants and approximately 5 to 25 percent (e.g., approximately 10 percent) of the plants in the random population can be the male fertile soybean plants. Following pollen transfer the seeds formed on the male sterile soybean plants are capable of forming the male fertile $F_1$ hybrid soybean plants, and the seeds formed on the restorer soybean plants are the result of self-pollination. The resulting seeds formed on the substantially random population of soybean plants next are harvested in bulk and can be planted in bulk by the grower.

The level of cross-pollination occurring in the random population of plants (discussed hereafter) can be visually observed by inspecting the resulting seeds or the plants produced when the resulting seeds are grown if one incorporates an appropriate genetic marker system into the parent plants which gives one appearance upon cross-pollination and another appearance upon self-pollination. The genetic marker can take the form of a recessive gene which expresses itself upon self-pollination, but which is dominated by another gene giving a different appearance when cross-pollination takes place. Under such circumstances the male fertile plants could be homozygous recessive for such trait and the male sterile plants homozygous dominant for such trait. For instance, the genetic marker can be a distinctive pubescence color (e.g., gray pubescence vs. tawny pubescence), flower color (e.g., white flowers vs. purple flowers), seed pod color (e.g., tan vs. brown pods), hilum appearance (e.g., yellow vs. black hilum or buff vs. black hilum), etc.

Alternatively, cytoplasmically male sterile soybean plants useful in the production of male fertile $F_1$ hybrid soybean plants can be maintained, perpetuated, and multiplied by planting a substantially uniform population of the same in pollinating proximity to a substantially uniform population of the maintainer soybean plants which when crossed with the male sterile soybean plants enable the formation of seeds on the cytoplasmically male sterile soybean plants which are capable of growing additional cytoplasmically male sterile plants. For instance, the two types of plants can be grown adjacent to each other as alternating strips as described earlier with respect to the production of male fertile $F_1$ hybrid seed. Following pollen transfer (as described hereafter) from the maintainer soybean plants to the male sterile soybean plants seeds are formed on the male sterile soybean plants. The maintainer plants are self-pollinated and seeds also form on them. At harvest time the seeds are selectively harvested from each of the substantially uniform plant populations. Accordingly, the seeds which are recovered from the male sterile soybean plants are a substantially homogeneous assemblage of seeds which upon growth yield cytoplasmically male sterile soybean plants. The seeds which are selectively recovered from the maintainer plants can be planted to produce additional maintainer plants or sold as a commercial soybean product.

Since the photosensitivity of soybean plants tends to vary among soybean varieties, it is important for best results that the parent soybean plants (i.e., the male sterile soybean plants and the male fertile soybean plants) each possess a day length sensitivity (i.e., a photoperiod response) which generally corresponds to that of the location (i.e., the latitude or distance from the equator) where the soybean plants are grown when carrying out the process of the present invention as well as to the area where the seed product is ultimately to be grown. For instance, the parent plants and the ultimate seed product preferably should possess a photosensitivity within plus or minus one maturity group unit of the locations where grown. Additionally, for optimum results the locations where grown should correspond exactly to the maturity groups of the plants involved.

See, Chapter 6 by Edgar E. Hartwig of "Soybeans: Improvement, Production, and Uses", American Society of Agronomy, Inc., Pages 189 to 190 (1973) which is herein incorporated by reference, for a discussion of soybean maturity group units and their significance. For instance, if a soybean variety which grows well at a southern latitude is grown at a northern latitude, the longer days may cause the soybean plants to grow excessively tall and to tend to lodge. Alternatively, if a soybean variety which grows well at a northern latitude is grown at a southern latitude, the shorter days may cause limited plant growth (i.e., height) and result in poor yields.

For best results soybean parent plants also are selected which inherently exhibit a propensity to flower during an overlapping time period at the location where grown. Such soybean plant parents may be either of the determinate type (i.e., flower over a period of approximately 20 to 25 days) or of the indeterminate type (i.e., flower over a period of approximately 35 to 50 days) so long as they flower simultaneously at a period of time during the summer. In a particularly preferred embodiment the flowering period for the male fertile soybean plant parent commences before the flowering period for the male sterile soybean plant parent and ends after the flowering period for the male sterile plant parent. Accordingly, the male fertile parent may be from a longer flowering indeterminate variety and the male sterile parent may be from a shorter flowering determinate variety. This will provide added insurance that pollen for the required cross-pollination will be available when the male sterile seed parent is ready to receive pollen.

In order to promote visitation by pollen-carrying bees (as discussed hereafter) the male sterile soybean plant parents can be selected for large blossom size to aid insect entry. Parent plants having flowers which are tightly cleistogamous are to be avoided since in such plants the flower keel tends not to open or the stigmas tend not to be exerted thereby making pollination difficult. Also, in order to promote visitation by pollen-carrying bees the flowers of both parents should be as attractive as possible to bees. Since, bees sometimes have a tendency to preferentially visit soybean flowers of a given color, it is preferred that the plants of each parent possess substantially the same flower coloration (e.g., be all purple or all white). In a particularly preferred embodiment the flowers of each parent are purple in coloration since this coloration often is found to be preferred by the bees which are relied upon to accomplish pollen transfer.

In accordance with the concept of the present invention, water is applied via irrigation to the seeds which produce the male sterile and male fertile soybean plants following planting as required to accomplish seed germination and normal plant growth up to at least the time of the onset of flower formation on each of the two plant types. The customary soybean planting times commonly are employed. The quantity of water applied will be influenced by the frequency and extent of natural rainfall (if any). The manner in which the irrigation water is applied may be varied and commonly will correspond to the irrigation technique that may be most conveniently implemented at the particular location which normally experiences limited natural rainfall. As will be apparent to those skilled in agronomic technology, the particular irrigation technique selected will also be influenced by the soil type encountered and its inherent water-holding capabilities. Light soils will inherently require lesser irrigation times and more frequent water applications. Representative irrigation techniques that may be selected include (1) sprinkler systems whereby water is sprayed and impacts upon the planting area from overhead through the air, (2) flooding systems whereby water confined by a levy or other means is caused to flow upon the surface of the soil and to substantially completely engulf the planting area, (3) furrow systems whereby a furrow is mechanically cut in the soil adjacent to the locations where the soybean plants are grown and is filled with water, etc. Sprinkler systems commonly have the advantage of using less water. In northeastern Arkansas commonly a flooding system will be employed. In western Texas commonly a furrow system or a sprinkler system will be employed. Also commonly, the water is applied via irrigation for a period of approximately 0.1 to 15 days (or more) prior to the withholding of irrigation water (as described hereafter). The duration of the time in which water is applied by irrigation will primarily be influenced by the natural rainfall (if any), the other weather conditions (e.g., heat and humidity) encountered, and the ability of the soil to hold water once irrigation is commenced. In any event, water is always applied as required via irrigation in sufficient quantities and at sufficient intervals to insure normal soybean plant growth up to at least the time when flowers are present on each of the parent plant types.

The application of water via irrigation promotes the normal vegetative growth of the soybean plants and flower formation. The nectar exuded by the resulting soybean flowers, when irrigation and/or natural rainfall is taking place, tends to be more dilute and is considerably less attractive to bees than that formed in the subsequent step of the present process (described hereafter) when irrigation water is withheld from the planting area.

The process of the present invention utilizes pollen-carrying bees to bring about the required cross-pollination of the parent soybean plants. At most growing areas honeybees are particularly effective in bringing about the desired cross-pollination. However, bees other than honeybees can alternatively be employed so long as they will reliably visit the soybean flowers at the appropriate time. For instance, leaf-cutter bees (i.e., *Megachile rotundata*) can be used. Also, naturally occurring bees other than honeybees and leaf-cutter bees (i.e., wild bees) advantageously may supplement the level of cross-pollination. Bees appear to visit soybean plants primarily in search of nectar and to a lesser extent for pollen that serves as a protein source for the bees. As bees collect nectar, they concomitantly serve to pick up and carry pollen from one soybean plant to another.

In a preferred embodiment of the process of the present invention, one or more honeybee hives are situated in pollinating proximity to the location where the parent soybean plants are being grown in order to insure the ample presence of sufficient pollen vectors. For instance, in a particularly preferred embodiment, honeybee hives are provided in pollinating proximity to the location where the parent soybean plants are being grown at a rate of at least 2 hives per acre (e.g., 2 to 3 hives per acre) of the parent soybean plants. When irrigation is accomplished by flooding, the hives may be situated on a small terrace above the water level. It further is preferred that a route be provided in the planting area to provide ready ingress and egress for the beekeepers having the responsibility of servicing the beehives. For best results, it is recommended that the honeybee hives be positioned so that the honeybees are not required to travel more than approximately one-quarter of a mile to visit the parent soybean plants. This tends to improve the foraging efficiency.

Since pollen serves as a protein source required by bees and soybean plants tend not to produce pollen in profuse quantities, it is preferred that a supplemental protein source for the pollen-carrying bees be provided in addition to the pollen formed on the male parent soybean plants in order to more fully support the pollen requirements of the pollen-carrying bees. Such supplemental protein source for the enrichment of the bee diet may take various forms. For instance, plants known to form pollen in relatively copious quantities (e.g., sorghum, sudan, pearl millet, etc.) can be grown nearby. Alternatively, a concentrated pollen source, such as pollen cakes available to beekeepers, can be placed in the vicinty of or within the honeybee hives.

Insecticides must be used with care in the planting area since adult bees may be killed and sometimes bees will refuse to visit fields which have been sprayed with insecticides. Accordingly, if insecticides are used they should possess a low killing potential for bees, and preferably be applied during the night or some other time when any beehives in the area are closed.

The overall process of the present invention provides a highly effective technique to bring about a high level of cross-pollination among the parent soybean plants. At an appropriate time when flowers are present on the parent soybean plants, irrigation water is withheld for a period of time during which no appreciable natural rainfall occurs in order to induce enhanced nectar flow within the flowers, which serves to render the flowers more attractive to bees. When irrigation water is withheld, the nectar flow within the soybean flowers increases substantially and the sugar component of the nectar becomes more concentrated and more aromatic. Such enhanced nectar flow is readily perceived by the bees that forage in the area and the bees are strongly attracted to the soybean flowers at a critical time in the life cycle of the soybean plants. Such increased bee visitation results in higher levels of the desired cross-pollination and seed set.

It is important that the period of time during which irrigation water is withheld not exceed that which can be well tolerated by the parent plants involved (i.e., not significantly impair the plant metabolism in a way which would interfere with the desired seed set and seed formation). The duration of the period in which irrigation water is withheld at a time when no appreciable natural rainfall occurs will be influenced by the environmental conditions (e.g., temperature, humidity, wind velocity, etc.) and the water-holding ability of the soil. In a preferred embodiment, the irrigation water is withheld for a period of at least 8 days (e.g., 10 to 15 days).

At the conclusion of the period during which irrigation water is withheld, the parent soybean plants may again be watered via irrigation to promote normal plant growth in order to insure the formation of the desired seeds that subsequently are harvested at the appropriate time in their maturity cycle. However, the process steps optionally may be repeated at least one time (e.g., 1 or 2 more times) during which irrigation water is applied, irrigation water is withheld, and additional cross-pollination by pollen-carrying bees is accomplished. Such repetition of the process steps may be carried out to particular advantage when the parent soybean plants are selected that inherently flower over an extended period of time (e.g., when both of the soybean parents have indeterminate flowering characteristics). For instance, when both soybean plant parents have indeterminate flowering characteristics, irrigation water commonly is withheld for a total of 2 or 3 times (or more) during the flowering period. However, when both soybean plant parents have determinate flowering characteristics, irrigation water commonly is withheld for a total of only 1 or 2 times during the flowering period.

The concept of the present invention provides a highly efficient technique for aiding the accomplishment of the desired cross-pollination of male sterile soybean plants with the aid of bees. The enhanced level of seed set made possible by the improved process of the present invention translates into greater and more reliable yields of the desired seeds (e.g., seeds capable of growing male fertile $F_1$ hybrid soybean plants or seeds capable of growing additional cytoplasmically male sterile soybean plants that are useful in the production of male fertile $F_1$ hybrid soybean plants).

Although the invention has been described with preferred embodiments, it is to be understood that variations and modifications may be resorted to as will be apparent to those skilled in the art. Such variations and modifications are to be considered within the purview and scope of the claims appended hereto.

I claim:

1. An improved process for the efficient production of seeds capable of growing male fertile $F_1$ hybrid *Glycine max* plants comprising:
   (a) growing at a location which normally experiences limited natural rainfall when soybean flowering occurs during the summer a substantially uniform population of male sterile soybean plants in pollinating proximity to a substantially uniform population of male fertile soybean plants which when crossed with said male sterile soybean plants enable the formation of seeds on said male sterile soybean plants which are capable of growing male fertile $F_1$ hybrid soybean plants,
   (b) applying water via irrigation to said substantially uniform populations of soybean plants of step (a) as required to promote normal plant growth up to at least the time of the onset of flower formation within each of said populations,
   (c) withholding irrigation water from said plants of said substantially uniform populations at a time when flowers are present within each of said substantially uniform populations for a period of time during which no appreciable natural rainfall occurs so as to induce enhanced nectar flow within said flowers which serves to render the flowers more attractive to bees,
   (d) crossing said male sterile soybean plants and said male fertile soybean plants with the aid of pollen-carrying bees which are attracted to said enhanced nectar flow whereby seeds are formed on said male sterile soybean plants, and
   (e) selectively recovering the seeds which have formed on said substantially uniform population of male sterile soybean plants.

2. An improved process for the efficient production of seeds capable of growing male fertile $F_1$ hybrid *Glycine max* plants according to claim 1 wherein said male sterile soybean plants of step (a) are cytoplasmically male sterile.

3. An improved process for the efficient production of seeds capable of growing male fertile $F_1$ hybrid *Glycine max* plants according to claim 1 wherein said male sterile soybean plants of step (a) are genetically male sterile.

4. An improved process for the efficient production of seeds capable of growing male fertile $F_1$ hybrid *Glycine max* plants according to claim 1 wherein said male sterile soybean plants of step (a) are rendered male sterile through the application of a gametocide.

5. An improved process for the efficient production of seeds capable of growing male fertile $F_1$ hybrid *Glycine max* plants according to claim 1 wherein the flowering period at said location for said male fertile soybean plants of step (a) commences before the flowering period for said male sterile soybean plants of step (a) and ends after the flowering period for said male sterile plants.

6. An improved process for the efficient production of seeds capable of growing male fertile $F_1$ hybrid *Glycine max* plants according to claim 1 wherein said substantially uniform populations of male sterile soybean plants and male fertile soybean plants are grown in alternating strips.

7. An improved process for the efficient production of seeds capable of growing male fertile $F_1$ hybrid *Glycine max* plants according to claim 1 which includes the additional step of selectively recovering seeds formed on said substantially uniform population of male fertile soybean plants grown in step (a).

8. An improved process for the efficient production of seeds capable of growing male fertile $F_1$ hybrid *Glycine max* plants according to claim 1 wherein said male fertile soybean plants grown in step (a) are a pure line variety.

9. An improved process for the efficient production of seeds capable of growing male fertile $F_1$ hybrid *Glycine max* plants according to claim 1 wherein said limited natural rainfall when soybean flowering occurs during the summer is normally less than 4 inches.

10. An improved process for the efficient production of seeds capable of growing male fertile $F_1$ hybrid *Glycine max* plants according to claim 1 wherein said limited natural rainfall when soybean flowering occurs during the summer is normally less than 2 inches.

11. An improved process for the efficient production of seeds capable of growing male fertile $F_1$ hybrid *Glycine max* plants according to claim 1 wherein said male sterile soybean plants and said male fertile soybean plants of step (a) each possess a day length sensitivity which generally corresponds to that of said location of step (a) and the area where the seeds capable of growing said male sterile $F_1$ hybrid plants are to be grown.

12. An improved process for the efficient production of seeds capable of growing male fertile $F_1$ hybrid *Glycine max* plants according to claim 1 wherein said male sterile soybean plants and said male fertile soybean plants of step (a) each possess substantially the same flower coloration.

13. An improved process for the efficient production of seeds capable of growing male fertile $F_1$ hybrid *Glycine max* plants according to claim 1 wherein said male sterile soybean plants and said male fertile soybean plants of step (a) each possess purple flowers.

14. An improved process for the efficient production of seeds capable of growing male fertile $F_1$ hybrid *Glycine max* plants according to claim 1 wherein water is applied by irrigation during step (b) for a period of approximately 0.1 to 15 days prior to the withholding of irrigation water in step (c).

15. An improved process for the efficient production of seeds capable of growing male fertile $F_1$ hybrid *Glycine max* plants according to claim 1 wherein water is withheld in step (c) for a period of at least 8 days.

16. An improved process for the efficient production of seeds capable of growing male fertile $F_1$ hybrid *Glycine max* plants according to claim 1 wherein water is withheld in step (c) for a period of approximately 10 to 15 days.

17. An improved process for the efficient production of seeds capable of growing male fertile $F_1$ hybrid *Glycine max* plants according to claim 1 wherein said pollen-carrying bees of step (d) are primarily honeybees.

18. An improved process for the efficient production of seeds capable of growing male fertile $F_1$ hybrid *Glycine max* plants according to claim 17 wherein honeybee hives are provided in pollinating proximity to said location of step (a) at a rate of at least 2 hives per acre of said substantially uniform populations of soybean plants.

19. An improved process for the efficient production of seeds capable of growing male fertile $F_1$ hybrid *Glycine max* plants according to claim 1 wherein following step (d), steps (b), (c) and (d) are successively repeated at least one time prior to step (e).

20. An improved process for the efficient production of seeds capable of growing male fertile $F_1$ hybrid *Glycine max* plants according to claim 1 wherein a supplemental pollen source for said pollen-carrying bees is provided in addition to the pollen formed on said male fertile soybean plants of step (a) in order to provide ample pollen to support said pollen-carrying bees.

21. An improved process for the efficient production of seeds capable of growing male fertile $F_1$ hybrid *Glycine max* plants comprising:
(a) growing at a location which normally experiences limited natural rainfall when soybean flowering occurs during the summer a substantially uniform population of male sterile soybean plants wherein said male sterility is attributable to the combination of an atypical Cms cytoplasm and two distinct pairs of recessive genes $r_1r_1$ and $r_2r_2$ in pollinating proximity to a substantially uniform population of male fertile soybean plants which possess at least one pair of dominant genes selected from the group consisting of $R_1R_1$ and $R_2R_2$ and which when crossed with said male sterile soybean plants enable the formation of seeds on said male sterile soybean plants which are capable of growing male fertile $F_1$ hybrid soybean plants,
(b) applying water via irrigation to said substantially uniform populations of soybean plants of step (a) as required to promote normal plant growth up to at least the time of the onset of flower formation within each of said populations,
(c) withholding irrigation water from said plants of said substantially uniform populations at a time when flowers are present within each of said substantially uniform populations for a period of time during which no appreciable natural rainfall occurs so as to induce enhanced nectar flow within said flowers which serves to render the flowers more attractive to bees,
(d) crossing said male sterile soybean plants and said male fertile soybean plants with the aid of pollen-carrying bees which are attracted to said enhanced nectar flow whereby seeds are formed on said male sterile soybean plants, and (e) selectively recovering the seeds which have formed on said substantially uniform population of male sterile soybean plants.

22. A process for the efficient production of seeds capable of growing male fertile $F_1$ hybrid *Glycine max* plants according to claim 21 wherein with respect to said male sterile soybean plants of step (a) said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes.

23. An improved process for the efficient production of seeds capable of growing male fertile $F_1$ hybrid *Glycine max* plants according to claim 22 wherein with respect to said male sterile soybean plants of step (a) said atypical Cms cytoplasm was derived through its female parent from a Mandarin cytoplasmic source, and in which said recessive genes $r_1r_1$ were derived through its male parent from a Dunfield germplasm base and in which said recessive genes $r_2r_2$ additionally were derived through its male parent from a Tokyo germplasm base.

24. An improved process for the efficient production of seeds capable of growing male fertile $F_1$ hybrid *Glycine max* plants according to claim 23 wherein with respect to said male sterile soybean plants of step (a) said atypical Cms cytoplasm was derived through its female parent from the Elf variety, and in which said recessive genes $r_1r_1$ were derived through its male parent from the Bedford variety, and in which said recessive genes $r_2r_2$ additionally were derived through its male parent from the Braxton variety.

25. An improved process for the efficient production of seeds capable of growing male fertile $F_1$ hybrid *Glycine max* plants according to claim 21 wherein the flowering period at said location for said male fertile soybean plants of step (a) commences before the flowering period for said male sterile soybean plants of step (a) and ends after the flowering period for said male sterile plants.

26. An improved process for the efficient production of seeds capable of growing male fertile $F_1$ hybrid *Glycine max* plants according to claim 21 wherein said substantially uniform populations of male sterile soybean plants and male fertile soybean plants are grown in alternating strips.

27. An improved process for the efficient production of seeds capable of growing male fertile $F_1$ hybrid *Glycine max* plants according to claim 21 which includes the additional step of selectively recovering seeds formed on said substantially uniform population of male fertile soybean plants grown in step (a).

28. An improved process for the efficient production of seeds capable of growing male fertile $F_1$ hybrid *Glycine max* plants according to claim 21 wherein said male fertile soybean plants grown in step (a) are a pure line variety.

29. An improved process for the efficient production of seeds capable of growing male fertile $F_1$ hybrid *Glycine max* plants according to claim 21 wherein said limited natural rainfall when soybean flowering occurs during the summer is normally less than 4 inches.

30. An improved process for the efficient production of seeds capable of growing male fertile $F_1$ hybrid *Glycine max* plants according to claim 21 wherein said limited natural rainfall when soybean flowering occurs during the summer is normally less than 2 inches.

31. An improved process for the efficient production of seeds capable of growing male fertile $F_1$ hybrid *Glycine max* plants according to claim 21 wherein said male sterile soybean plants and said male fertile soybean plants of step (a) each possess a day length sensitivity which generally corresponds to that of said location of step (a) and the area where the seeds capable of growing said male sterile $F_1$ hybrid plants are to be grown.

32. An improved process for the efficient production of seeds capable of growing male fertile $F_1$ hybrid *Glycine max* plants according to claim 21 wherein said male sterile soybean plants and said male fertile soybean plants of step (a) each possess substantially the same flower coloration.

33. An improved process for the efficient production of seeds capable of growing male fertile $F_1$ hybrid *Glycine max* plants according to claim 21 wherein said male sterile soybean plants and said male fertile soybean plants of step (a) each possess purple flowers.

34. An improved process for the efficient production of seeds capable of growing male fertile $F_1$ hybrid *Glycine max* plants according to claim 21 wherein water is applied by irrigation during step (b) for a period of approximately 0.1 to 15 days prior to the withholding of irrigation water in step (c).

35. An improved process for the efficient production of seeds capable of growing male fertile $F_1$ hybrid *Glycine max* plants according to claim 21 wherein water is withheld in step (c) for a period of at least 8 days.

36. An improved process for the efficient production of seeds capable of growing male fertile $F_1$ hybrid *Glycine max* plants according to claim 21 wherein water is withheld in step (c) for a period of approximately 10 to 15 days.

37. An improved process for the efficient production of seeds capable of growing male fertile $F_1$ hybrid *Glycine max* plants according to claim 21 wherein said pollen-carrying bees of step (d) are primarily honeybees.

38. An improved process for the efficient production of seeds capable of growing male fertile $F_1$ hybrid *Glycine max* plants according to claim 37 wherein honeybee hives are provided in pollinating proximity to said location of step (a) at a rate of at least 2 hives per acre of said substantially uniform populations of soybean plants.

39. An improved process for the efficient production of seeds capable of growing male fertile $F_1$ hybrid *Glycine max* plants according to claim 21 wherein following step (d), steps (b), (c), and (d) are successively repeated at least one time prior to step (e).

40. An improved process for the efficient production of seeds capable of growing male fertile $F_1$ hybrid *Glycine max* plants according to claim 21 wherein a supplemental pollen source for said pollen-carrying bees is provided in addition to the pollen formed on said male fertile soybean plants of step (a) in order to provide ample pollen to support said pollen-carrying bees.

41. An improved process for the efficient production of a binary seed blend containing a substantial proportion of seeds capable of growing male fertile $F_1$ hybrid *Glycine max* plants comprising:

(a) growing at a location which normally experiences limited natural rainfall when soybean flowering occurs during the summer a substantially random population of male sterile soybean plants and male fertile soybean plants which when crossed with said male sterile soybean plants enable the formation of seeds on said male sterile soybean plants which are capable of growing male fertile $F_1$ hybrid soybean plants, (b) applying water via irrigation to said substantially random population of soybean plants of step (a) as required to promote normal plant growth up to at least the time of the onset of flower formation, (c) withholding irrigation water from said plants of said substantially random population at a time when flowers are present for a period of time during which no appreciable natural rainfall occurs so as to induce enhanced nectar flow within said flowers which serves to render the flowers more attractive to bees, (d) pollinating said substantially random population of soybean plants with the aid of pollen-carrying bees which are attracted to said enhanced nectar flow whereby seeds are formed on said male sterile plants which are capable of growing male fertile $F_1$ hybrid soybean plants and seeds are formed on said male fertile soybean plants as a result of self-pollination, and (e) recovering seeds which have formed on said substantially random population of soybean plants.

42. An improved process for the efficient production of a binary seed blend containing a substantial proportion of seeds capable of growing male fertile $F_1$ hybrid Glycine max plants according to claim 41 wherein said male sterile soybean plants of step (a) are cytoplasmically male sterile.

43. An improved process for the efficient production of a binary seed blend containing a substantial proportion of seeds capable of growing male fertile $F_1$ hybrid Glycine max plants according to claim 41 wherein said male sterile soybean plants of step (a) are genetically male sterile.

44. An improved process for the efficient production of seeds capable of growing male fertile $F_1$ hybrid Glycine max plants according to claim 41 wherein the flowering period at said location for said male fertile soybean plants of step (a) commences before the flowering period for said male sterile soybean plants of step (a) and ends after the flowering period for said male sterile plants.

45. An improved process for the efficient production of a binary seed blend containing a substantial proportion of seeds capable of growing male fertile $F_1$ hybrid Glycine max plants according to claim 41 wherein said male fertile soybean plants grown in step (a) are a pure line variety.

46. An improved process for the efficient production of a binary seed blend containing a substantial proportion of seeds capable of growing male fertile $F_1$ hybrid Glycine max plants according to claim 41 wherein said limited natural rainfall when soybean flowering occurs during the summer is normally less than 4 inches.

47. An improved process for the efficient production of a binary seed blend containing a substantial proportion of seeds capable of growing male fertile $F_1$ hybrid Glycine max plants according to claim 41 wherein said limited natural rainfall when soybean flowering occurs during the summer is normally less than 2 inches.

48. An improved process for the efficient production of a binary seed blend containing a substantial proportion of seeds capable of growing male fertile $F_1$ hybrid Glycine max plants according to claim 41 wherein said male sterile soybean plants and said male fertile soybean plants of step (a) each possess a day length sensitivity which generally corresponds to that of said location of step (a) and the area where the seeds capable of growing said male sterile $F_1$ hybrid plants are to be grown.

49. An improved process for the efficient production of a binary seed blend containing a substantial proportion of seeds capable of growing male fertile $F_1$ hybrid Glycine max plants according to claim 41 wherein said male sterile soybean plants and said male fertile soybean plants of step (a) each possess substantially the same flower coloration.

50. An improved process for the efficient production of a binary seed blend containing a substantial proportion of seeds capable of growing male fertile $F_1$ hybrid Glycine max plants according to claim 41 wherein said male sterile soybean plants and said male fertile soybean plants of step (a) each possess purple flowers.

51. An improved process for the efficient production of a binary seed blend containing a substantial proportion of seeds capable of growing male fertile $F_1$ hybrid Glycine max plants according to claim 41 wherein water is applied by irrigation during step (b) for a period of approximately 0.1 to 15 days prior to the withholding of irrigation water in step (c).

52. An improved process for the efficient production of a binary seed blend containing a substantial proportion of seeds capable of growing male fertile $F_1$ hybrid Glycine max plants according to claim 41 wherein water is withheld in step (c) for a period of at least 8 days.

53. An improved process for the efficient production of a binary seed blend containing a substantial proportion of seeds capable of growing male fertile $F_1$ hybrid Glycine max plants according to claim 41 wherein water is withheld in step (c) for a period of approximately 10 to 15 days.

54. An improved process for the efficient production of a binary seed blend containing a substantial proportion of seeds capable of growing male fertile $F_1$ hybrid Glycine max plants according to claim 41 wherein said pollen-carrying bees of step (d) are primarily honeybees.

55. An improved process for the efficient production of seeds capable of growing male fertile $F_1$ hybrid Glycine max plants according to claim 54 wherein honeybee hives are provided in pollinating proximity to said location of step (a) at a rate of at least 2 hives per acre of said substantially random population of soybean plants.

56. An improved process for the efficient production of a binary seed blend containing a substantial proportion of seeds capable of growing male fertile $F_1$ hybrid Glycine max plants according to claim 41 wherein following step (d), steps (b), (c) and (d) are successively repeated at least one time prior to step (e).

57. An improved process for the efficient production of a binary seed blend containing a substantial proportion of seeds capable of growing male fertile $F_1$ hybrid Glycine max plants according to claim 41 wherein a supplemental pollen source for said polley-carrying bees is provided in addition to the pollen formed on said male fertile soybean plants of step (a) in order to provide ample pollen to support said pollen-carrying bees.

58. An improved process for the efficient production of a binary seed blend containing a substantial proportion of seeds capable of growing male fertile $F_1$ hybrid *Glycine max* plants comprising:
  (a) growing at a location which normally experiences limited natural rainfall when soybean flowering occurs during the summer a substantially random population of (i) male sterile soybean plants wherein said male sterility is attributable to the combination of an atypical Cms cytoplasm and two distinct pairs of recessive genes $r_1r_1$ and $r_2r_2$, and (ii) male fertile soybean plants which possess at least one pair of dominant genes selected from the group consisting of $R_1R_1$ and $R_2R_2$ and which when crossed with said male sterile soybean plants enable the formation of seeds on said male sterile soybean plants which are capable of growing male fertile $F_1$ hybrid soybean plants,
  (b) applying water via irrigation to said substantially random population of soybean plants of step (a) as required to promote normal plant growth up to at least the time of the onset of flower formation,
  (c) withholding irrigation water from said plants of said substantially random population at a time when flowers are present for a period of time during which no appreciable natural rainfall occurs so as to induce enhanced nectar flow within said flowers which serves to render the flowers more attractive to bees,
  (d) crossing said male sterile soybean plants and said male fertile soybean plants with the aid of pollen-carrying bees which are attracted to said enhanced nectar flow whereby seeds are formed on said male sterile soybean plants, and
  (e) recovering seeds which have formed on said substantially random population of soybean plants.

59. An improved process for the efficient production of a binary seed blend containing a substantial proportion of seeds capable of growing male fertile $F_1$ hybrid *Glycine max* plants according to claim 58 wherein with respect to said male sterile soybean plants of step (a) said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes.

60. An improved process for the efficient production of a binary seed blend containing a substantial proportion of seeds capable of growing male fertile $F_1$ hybrid *Glycine max* plants according to claim 59 wherein with respect to said male sterile soybean plants of step (a) said atypical Cms cytoplasm was derived through its female parent from a Mandarin cytoplasmic source, and in which said recessive genes $r_1r_1$ were derived through its male parent from a Dunfield germplasm base and in which said recessive genes $r_2r_2$ additionally were derived through its male parent from a Tokyo germplasm base.

61. An improved process for the efficient production of a binary seed blend containing a substantial proportion of seeds capable of growing male fertile $F_1$ hybrid *Glycine max* plants according to claim 60 wherein with respect to said male sterile soybean plants of step (a) said atypical Cms cytoplasm was derived through its female parent from the Elf variety, and in which said recessive genes $r_1r_1$ were derived through its male parent from the Bedford variety, and in which said recessive genes $r_2r_2$ additionally were derived through its male parent from the Braxton variety.

62. An improved process for the efficient production of seeds capable of growing male fertile $F_1$ hybrid *Glycine max* plants according to claim 58 wherein the flowering period at said location for said male fertile soybean plants of step (a) commences before the flowering period for said male sterile soybean plants of step (a) and ends after the flowering period for said male sterile plants.

63. An improved process for the efficient production of a binary seed blend containing a substantial proportion of seeds capable of growing male fertile $F_1$ hybrid *Glycine max* plants according to claim 58 wherein said male fertile soybean plants grown in step (a) are a pure line variety.

64. An improved process for the efficient production of a binary seed blend containing a substantial proportion of seeds capable of growing male fertile $F_1$ hybrid *Glycine max* plants according to claim 58 wherein said limited natural rainfall when soybean flowering occurs during the summer is normally less than 4 inches.

65. An improved process for the efficient production of a binary seed blend containing a substantial proportion of seeds capable of growing male fertile $F_1$ hybrid *Glycine max* plants according to claim 58 wherein said limited natural rainfall when soybean flowering occurs during the summer is normally less than 2 inches.

66. An improved process for the efficient production of a binary seed blend containing a substantial proportion of seeds capable of growing male fertile $F_1$ hybrid *Glycine max* plants according to claim 58 wherein said male sterile soybean plants and said male fertile soybean plants of step (a) each possess a day length sensitivity which generally corresponds to that of said location of step (a) and the area where the seeds capable of growing said male sterile $F_1$ hybrid plants are to be grown.

67. An improved process for the efficient production of a binary seed blend containing a substantial proportion of seeds capable of growing male fertile $F_1$ hybrid *Glycine max* plants according to claim 58 wherein said male sterile soybean plants and said male fertile soybean plants of step (a) each possess substantially the same flower coloration.

68. An improved process for the efficient production of a binary seed blend containing a substantial proportion of seeds capable of growing male fertile $F_1$ hybrid *Glycine max* plants according to claim 58 wherein said male sterile soybean plants and said male fertile soybean plants of step (a) each possess purple flowers.

69. An improved process for the efficient production of a binary seed blend containing a substantial proportion of seeds capable of growing male fertile $F_1$ hybrid *Glycine max* plants according to claim 58 wherein water is applied by irrigation during step (b) for a period of approximately 0.1 to 15 days prior to the withholding of irrigation water in step (c).

70. An improved process for the efficient production of a binary seed blend containing a substantial proportion of seeds capable of growing male fertile $F_1$ hybrid *Glycine max* plants according to claim 58 wherein water is withheld in step (c) for a period of at least 8 days.

71. An improved process for the efficient production of a binary seed blend containing a substantial proportion of seeds capable of growing male fertile $F_1$ hybrid *Glycine max* plants according to claim 58 wherein water is withheld in step (c) for a period of approximately 10 to 15 days.

72. An improved process for the efficient production of a binary seed blend containing a substantial proportion of seeds capable of growing male fertile $F_1$ hybrid *Glycine max* plants according to claim 58 wherein said pollen-carrying bees of step (d) are primarily honeybees.

73. An improved process for the efficient production of seeds capable of growing male fertile $F_1$ hybrid *Glycine max* plants according to claim 72 wherein honeybee hives are provided in pollinating proximity to said location of step (a) at a rate of at least 2 hives per acre of said substantially random population of soybean plants.

74. An improved process for the efficient production of a binary seed blend containing a substantial proportion of seeds capable of growing male fertile $F_1$ hybrid *Glycine max* plants according to claim 58 wherein following step (d), steps (b), (c), and (d) are successively repeated at least one time prior to step (e).

75. An improved process for the efficient production of a binary seed blend containing a substantial proportion of seeds capable of growing male fertile $F_1$ hybrid *Glycine max* plants according to claim 58 wherein a supplemental pollen source for said pollen carrying bees is provided in addition to the pollen formed on said male fertile soybean plants of step (a) in order to provide ample pollen to support said pollen-carrying bees.

76. An improved process for maintaining male sterile *Glycine max* plants useful in the production of male fertile $F_1$ hybrid soybean plants comprising:

(a) growing at a location which normally experiences limited natural rainfall when soybean flowering occurs during the summer a substantially uniform population of cytoplasmically male sterile soybean plants in pollinating proximity to a substantially uniform population of male fertile maintainer soybean plants which when crossed with said cytoplasmically male sterile soybean plants enable the formation of seeds on said cytoplasmically male sterile plants which are capable of growing additional cytoplasmically male sterile plants, (b) applying water via irrigation to said substantially uniform populations of soybean plants of step (a) as required to promote normal plant growth up to at least the time of the onset of flower formation within each of said populations, (c) withholding irrigation water from said plants of said substantially uniform populations at a time when flowers are present within each of said substantially uniform populations for a period of time during which no appreciable natural rainfall occurs so as to induce enhanced nectar flow within said flowers which serves to render the flowers more attractive to bees, (d) crossing said cytoplasmically male sterile soybean plants and said male fertile maintainer soybean plants with the aid of pollen-carrying bees which are attracted to said enhanced nectar flow whereby seeds are formed on said male sterile soybean plants, and (e) selectively recovering the seeds which have formed on said substantially uniform population of cytoplasmically male sterile soybean plants.

77. An improved process for the efficient production of seeds capable of growing male fertile $F_1$ hybrid *Glycine max* plants according to claim 76 wherein the flowering period at said location for said male fertile soybean plants of step (a) commences before the flowering period for said male sterile soybean plants of step (a) and ends after the flowering period for said male sterile plants.

78. An improved process for maintaining male sterile *Glycine max* plants useful in the production of male fertile $F_1$ hybrid soybean plants according to claim 76 wherein said substantially uniform populations of cytoplasmically male sterile soybean plants and male fertile soybean plants are grown in alternating strips.

79. An improved process for maintaining male sterile *Glycine max* plants useful in the production of male fertile $F_1$ hybrid soybean plants according to claim 76 which includes the additional step of selectively recovering seeds formed on said substantially uniform population of male fertile maintainer soybean plants grown in step (a).

80. An improved process for maintaining male sterile *Glycine max* plants useful in the production of male fertile $F_1$ hybrid soybean plants according to claim 76 wherein said male fertile maintainer soybean plants grown in step (a) are a pure line variety.

81. An improved process for maintaining male sterile *Glycine max* plants useful in the production of male fertile $F_1$ hybrid soybean plants according to claim 76 wherein said limited natural rainfall when soybean flowering occurs during the summer is normally less than 4 inches.

82. An improved process for maintaining male sterile *Glycine max* plants useful in the production of male fertile $F_1$ hybrid soybean plants according to claim 76 wherein said limited natural rainfall when soybean flowering occurs during the summer is normally less than 2 inches.

83. An improved process for maintaining male sterile *Glycine max* plants useful in the production of male fertile $F_1$ hybrid soybean plants according to claim 76 wherein said cytoplasmically male sterile soybean plants and said male fertile maintainer soybean plants of step (a) each possess a day length sensitivity which generally corresponds to that of said location of step (a) and the area where the seeds capable of growing said cytoplasmically male sterile soybean plants are to be grown.

84. An improved process for maintaining male sterile *Glycine max* plants useful in the production of male fertile $F_1$ hybrid soybean plants according to claim 76 wherein said cytoplasmically male sterile soybean plants and said male fertile maintainer soybean plants of step (a) each possess substantially the same flower coloration.

85. An improved process for maintaining male sterile *Glycine max* plants useful in the production of male fertile $F_1$ hybrid soybean plants according to claim 76 wherein said cytoplasmically male sterile soybean plants and said male fertile maintainer soybean plants of step (a) each possess purple flowers.

86. An improved process for maintaining male sterile *Glycine max* plants useful in the production of male fertile $F_1$ hybrid soybean plants according to claim 76 wherein water is applied by irrigation during step (b) for a period of approximately 0.1 to 15 days prior to the withholding of irrigation water in step (c).

87. An improved process for maintaining male sterile *Glycine max* plants useful in the production of male fertile $F_1$ hybrid soybean plants according to claim 76 wherein water is withheld in step (c) for a period of at least 8 days.

88. An improved process for maintaining male sterile *Glycine max* plants useful in the production of male fertile $F_1$ hybrid soybean plants according to claim 76 wherein water is withheld in step (c) for a period of approximately 10 to 15 days.

89. An improved process for maintaining male sterile *Glycine max* plants useful in the production of male fertile $F_1$ hybrid soybean plants according to claim 76 wherein said pollen-carrying bees of step (d) are primarily honeybees.

90. An improved process for the efficient production of seeds capable of growing male fertile $F_1$ hybrid *Glycine max* plants according to claim 89 wherein honeybee hives are provided in pollinating proximity to said location of step (a) at a rate of at least 2 hives per acre of said substantially uniform populations of soybean plants.

91. An improved process for maintaining male sterile *Glycine max* plants useful in the production of male fertile $F_1$ hybrid soybean plants according to claim 76 wherein following step (d), steps (b), (c), and (d) are successively repeated at least one time prior to step (e).

92. An improved process for maintaining male sterile *Glycine max* plants useful in the production of male fertile $F_1$ hybrid soybean plants according to claim 76 wherein a supplemental pollen source for said pollen-carrying bees is provided in addition to the pollen formed on said male fertile maintainer soybean plants of step (a) in order to provide ample pollen to support said pollen-carrying bees.

93. An improved process for maintaining male sterile *Glycine max* plants useful in the production of male fertile $F_1$ hybrid soybean plants comprising:
  (a) growing at a location which normally experiences limited natural rainfall when soybean flowering occurs during the summer a substantially uniform population of male sterile soybean plants wherein said male sterility is attributable to the combination of an atypical Cms cytoplasm and two distinct pairs of recessive genes $r_1r_1$ and $r_2r_2$ in pollinating proximity to a substantially uniform population of male fertile maintainer soybean plants which possess an N cytoplasm and two distinct pairs of recessive genes $r_1r_1$ and $r_2r_2$, which when crossed with said male sterile soybean plants enable the formation of seeds on said male sterile plants which are oapable of growing additional male sterile plants,
  (b) applying water via irrigation to said substantially uniform populations of soybean plants of step (a) as required to promote normal plant growth up to at least the time of the onset of flower formation within each of said populations,
  (c) withholding irrigation water from said plants of said substantially uniform populations at a time when flowers are present within each of said substantially uniform populations for a period of time during which no appreciable natural rainfall occurs so as to induce enhanced nectar flow within said flowers which serves to render the flowers more attractive to bees,
  (d) crossing said male sterile soybean plants and said male fertile maintainer soybean plants with the aid of pollen-carrying bees which are attracted to said enhanced nectar flow whereby seeds are formed on said male sterile soybean plants, and
  (e) selectively recovering the seeds which have formed on said substantially uniform population of sterile soybean plants.

94. An improved process for maintaining male sterile *Glycine max* plants useful in the production of male fertile $F_1$ hybrid soybean plants according to claim 93 wherein with respect to said male sterile soybean plants of step (a) said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes.

95. An improved process for maintaining male sterile *Glycine max* plants useful in the production of male fertile $F_1$ hybrid soybean plants according to claim 94 wherein with respect to said male sterile soybean plants of step (a) said atypical Cms cytoplasm was derived through its female parent from a Mandarin cytoplasmic source, and in which said recessive genes $r_1r_1$ were derived through its male parent from a Dunfield germplasm base and in which said recessive genes $r_2r_2$ additionally were derived through its male parent from a Tokyo germplasm base.

96. An improved process for maintaining male sterile *Glycine max* plants useful in the production of male fertile $F_1$ hybrid soybean plants according to claim 95 wherein with respect to said male sterile soybean plants of step (a) said atypical Cms cytoplasm was derived through its female parent from the Elf variety, and in which said recessive genes $r_1r_1$ were derived through its male parent from the Bedford variety, and in which said recessive genes $r_2r_2$ additionally were derived through its male parent from the Braxton variety.

97. An improved process for the efficient production of seeds capable of growing male fertile $F_1$ hybrid *Glycine max* plants according to claim 93 wherein the flowering period at said location for said male fertile soybean plants of step (a) commences before the flowering period for said male sterile soybean plants of step (a) and ends after the flowering period for said male sterile plants.

98. An improved process for maintaining male sterile *Glycine max* plants useful in the production of male fertile $F_1$ hybrid soybean plants according to claim 93 wherein said substantially uniform populations of male sterile soybean plants and male fertile maintainer soybean plants are grown in alternating strips.

99. An improved process for maintaining male sterile *Glycine max* plants useful in the production of male fertile $F_1$ hybrid soybean plants according to claim 93 which includes the additional step of selectively recovering seeds formed on said substantially uniform population of male fertile maintainer soybean plants grown in step (a).

100. An improved process for maintaining male sterile *Glycine max* plants useful in the production of male fertile $F_1$ hybrid soybean plants according to claim 93 wherein said male fertile maintainer soybean plants grown in step (a) are a pure line variety.

101. An improved process for maintaining male sterile *Glycine max* useful in the production of male fertile $F_1$ hybrid soybean plants according to claim 93 wherein said limited natural rainfall when soybean flowering occurs during the summer is normally less than 4 inches.

102. An improved process for maintaining male sterile *Glycine max* plants useful in the production of male fertile F$_1$ hybrid soybean plants according to claim 93 wherein said limited natural rainfall when soybean flowering occurs during the summer is normally less than 2 inches.

103. An improved process for maintaining male sterile *Glycine max* plants useful in the production of male fertile F$_1$ hybrid soybean plants according to claim 93 wherein said male sterile soybean plants and said male fertile maintainer soybean plants of step (a) each possess a day length sensitivity which generally corresponds to that of said location of step (a) and the area where the seeds capable of growing said male sterile soybean plants are to be grown.

104. An improved process for maintaining male sterile *Glycine max* plants useful in the production of male fertile F$_1$ hybrid soybean plants according to claim 93 wherein said male sterile soybean plants and said male fertile maintainer soybean plants of step (a) each possess substantially the same flower coloration.

105. An improved process for maintaining male sterile *Glycine max* plants useful in the production of male fertile F$_1$ hybrid soybean plants according to claim 93 wherein said male sterile soybean plants and said male fertile maintainer soybean plants of step (a) each possess purple flowers.

106. An improved process for maintaining male sterile *Glycine max* plants useful in the production of male fertile F$_1$ hybrid soybean plants according to claim 93 wherein water is applied by irrigation during step (b) for a period of approximately 0.1 to 15 days prior to the withholding of irrigation water in step (c).

107. An improved process for maintaining male sterile *Glycine max* plants useful in the production of male fertile F$_1$ hybrid soybean plants according to claim 93 wherein water is withheld in step (c) for a period of at least 8 days.

108. An improved process for maintaining male sterile *Glycine max* plants useful in the production, of male fertile F$_1$ hybrid soybean plants according to claim 93 wherein water is withheld in step (c) for a period of approximately 10 to 15 days.

109. An improved process for maintaining male sterile *Glycine max* plants useful in the production of male fertile F$_1$ hybrid soybean plants according to claim 93 wherein said pollen-carrying bees of step (d) are primarily honeybees.

110. An improved process for the efficient production of seeds capable of growing male fertile F$_1$ hybrid *Glycine max* plants according to claim 109 wherein honeybee hives are provided in pollinating proximity to said location of step (a) at a rate of at least 2 hives per acre of said substantially uniform populations of soybean plants.

111. An improved process for maintaining male sterile *Glycine max* plants useful in the production of male fertile F$_1$ hybrid soybean plants according to claim 93 wherein following step (d), steps (b), (c), and (d) are successively repeated at least one time prior to step (e).

112. An improved process for maintaining male sterile *Glycine max* plants useful in the production of male fertile F$_1$ hybrid soybean plants according to claim 93 wherein a supplemental pollen source for said pollen-carrying bees is provided in addition to the pollen formed on said male fertile maintainer soybean plants of step (a) in order to provide ample pollen to support said pollen-carrying bees.

* * * * *